(12) United States Patent
Szu et al.

(10) Patent No.: US 9,366,633 B2
(45) Date of Patent: Jun. 14, 2016

(54) APPARATUS BASED ON A HAND-HELD RAMAN LASER DEVICE INTEGRATING MULTIPLE FUNCTIONAL SYSTEMS FOR DISTANT LIFE-DEATH DETERMINATION

(71) Applicant: The United States of America, as represented by the Secretary of the Army, Washington, DC (US)

(72) Inventors: Harold H. Szu, Bethesda, MD (US); Lein W. Ma, Lorton, VA (US); James A. Hutchinson, Springfield, VA (US)

(73) Assignee: THE UNITED STATES OF AMERICA, AS REPRESENTED BY THE SECRETARY OF THE ARMY, Washington, DC (US)

( * ) Notice: Subject to any disclaimer, the term of this patent is extended or adjusted under 35 U.S.C. 154(b) by 113 days.

(21) Appl. No.: 14/477,898

(22) Filed: Sep. 5, 2014

(65) Prior Publication Data

US 2015/0323464 A1 Nov. 12, 2015

Related U.S. Application Data

(62) Division of application No. 13/170,434, filed on Jun. 28, 2011, now Pat. No. 8,854,618.

(51) Int. Cl.
*G01J 3/44* (2006.01)
*G01N 21/65* (2006.01)
*A61B 5/00* (2006.01)
*G01N 1/00* (2006.01)

(52) U.S. Cl.
CPC .............. *G01N 21/65* (2013.01); *A61B 5/0075* (2013.01); *A61B 5/7264* (2013.01); *G01N 2001/007* (2013.01); *G01N 2201/06113* (2013.01); *G01N 2201/12* (2013.01)

(58) Field of Classification Search
CPC .... A61B 5/0075; A61B 5/7264; G01N 21/65; G01N 2001/007
See application file for complete search history.

(56) References Cited

U.S. PATENT DOCUMENTS 5,162,232 A 11/1992 Vass
7,505,128 B2 3/2009 Zribi et al.
(Continued)

OTHER PUBLICATIONS

Chen et al., "Laser Doppler Vibrotometry Measures of Physiological Function: Evaluation of Biometric Capabilities," Sep. 2010, IEEE, vol. 5, No. 3, pp. 449-460.

*Primary Examiner* — Kara E Geisel
*Assistant Examiner* — Maurice Smith
(74) *Attorney, Agent, or Firm* — Richard J. Kim

(57) ABSTRACT

Multiple functional systems are integrated to configure a portable handheld decision-aid device for first responder medics. Fuzzy membership functions of "life" and "death" are used to determine the status of fallen people using remote measurements. EO/IR cameras can be used to detect and identify casualties in a mass injury situation, while also estimating body temperature. Using the temperature, along with the remote estimation of a second vital sign, the life membership proportion can be estimated from the ground truth by using a 2D projection of stable vital signs. The other fuzzy membership function, death, can be estimated by the presence or absence of peri-mortem and post-mortem molecules. These molecules are only released after death and provide a certain indication of death. Solid state UV laser resonance Raman backscattering from these molecules allows the device to analyze the molecules present in a plume around the casualty.

14 Claims, 14 Drawing Sheets

(56) References Cited

U.S. PATENT DOCUMENTS

| | | | |
|---|---|---|---|
| 8,582,089 B2* | 11/2013 | Nelson | G01J 3/02 356/73 |
| 2004/0039269 A1 | 2/2004 | Ward et al. | |
| 2005/0085740 A1 | 4/2005 | Davis et al. | |
| 2006/0073483 A1 | 4/2006 | White et al. | |
| 2006/0074282 A1* | 4/2006 | Ward | A61B 5/0071 600/310 |
| 2006/0160134 A1 | 7/2006 | Melker et al. | |
| 2007/0268485 A1 | 11/2007 | Polonskiy et al. | |
| 2010/0085567 A1 | 4/2010 | Dottery et al. | |

* cited by examiner

|  |  | Blood Pressure (Systolic/Diastolic in kPa) | | | | |
|---|---|---|---|---|---|---|
|  |  | <12.0/8.0 | 12.0/8.0 to 13.3/8.7 | 13.3/8.7 to 17.3/11.3 | 17.3/11.3 to 18.7/12.0 | >18.7/12.0 |
| Body Temperature (°F) | <95 | 100% Unstable | 50% Stable 50% Unstable | 60% Stable 40% Unstable | 50% Stable 50% Unstable | 100% Unstable |
| | 95-97.8 | 80% Unstable | 60% Stable 40% Unstable | 75% Stable 25% Unstable | 60% Stable 40% Unstable | 80% Unstable |
| | 97.8-99.1 | 30% Stable 70% Unstable | 90% Stable | 100% Stable | 90% Stable | 30% Stable 70% Unstable |
| | 99.1-102 | 60% Unstable | 80% Stable 20% Unstable | 90% Stable 10% Unstable | 80% Stable 20% Unstable | 40% Stable 60% Unstable |
| | 102-104 | 80% Unstable | 40% Stable 60% Unstable | 85% Stable 15% Unstable | 40% Stable 60% Unstable | 20% Stable 80% Unstable |
| | >104 | 100% Unstable | 25% Stable 75% Unstable | 75% Stable 25% Unstable | 20% Stable 80% Unstable | 100% Unstable |

Figure 5

|  |  | Blood Pressure (Systolic/Diastolic in kPa) | | | | |
| --- | --- | --- | --- | --- | --- | --- |
|  |  | <12.0/8.0 | 12.0/8.0 to 13.3/8.7 | 13.3/8.7 to 17.3/11.3 | 17.3/11.3 to 18.7/12.0 | >18.7/12.0 |
| Body Temp- erature (°F) | <95 | 100% Unstable | 50% Stable 50% Unstable | 60% Stable 40% Unstable | 50% Stable 50% Unstable | 100% Unstable |
|  | 95-97.8 | 80% Unstable | 60% Stable 40% Unstable | 75% Stable 25% Unstable | 60% Stable 40% Unstable | 80% Unstable |
|  | 97.8-99.1 | 30% Stable 70% Unstable | 90% Stable | 100% Stable | 90% Stable | 30% Stable 70% Unstable |
|  | 99.1-102 | 60% Unstable | 80% Stable 20% Unstable | 90% Stable 10% Unstable | 80% Stable 20% Unstable | 40% Stable 60% Unstable |
|  | 102-104 | 80% Unstable | 40% Stable 60% Unstable | 85% Stable 15% Unstable | 40% Stable 60% Unstable | 20% Stable 80% Unstable |
|  | >104 | 100% Unstable | 25% Stable 75% Unstable | 75% Stable 25% Unstable | 20% Stable 80% Unstable | 100% Unstable |

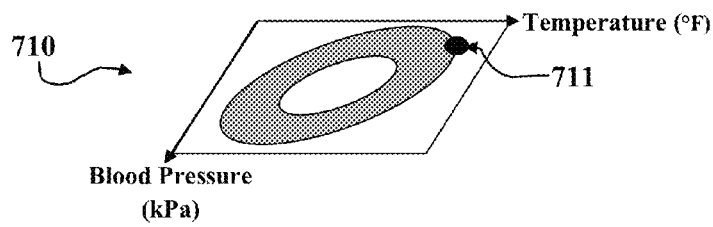

Figure 7

APPARATUS BASED ON A HAND-HELD RAMAN LASER DEVICE INTEGRATING MULTIPLE FUNCTIONAL SYSTEMS FOR DISTANT LIFE-DEATH DETERMINATION

REFERENCE TO RELATED APPLICATIONS

This is a divisional patent application of copending application Ser. No. 13/170,434, filed Jun. 28, 2011, entitled "Hand-Held Raman Laser Device for Distant Life-Death Determination by Molecular Peri-Mortem Plume Fuzzy Membership Function." The aforementioned application is hereby incorporated herein by reference.

GOVERNMENT INTEREST

The invention described herein may be manufactured, used, sold, imported, and/or licensed by or for the Government of the United States of America.

FIELD OF THE INVENTION

This invention relates in general to molecular plume detection, and more particularly, to a Raman laser device for molecular peri-mortem plume detection.

BACKGROUND OF THE INVENTION

An in-situ tissue sampling by means of chemical mass spectrum and gas chromatography analysis has been proposed by Dr. Vass at Oak Ridge Body Farm to determine the time after death. (See, e.g., U.S. Pat. No. 5,162,232 Vass.) There is a need to determine the timeline of death from a distance. In wars, many medics die while trying to save an already dead comrade, whether it is from getting caught in the middle of the fighting or from a baited body that contains hidden danger designed to create more injuries. Mass casualties and disasters in homeland security scenarios are also associated with contagious or radioactive hazardous conditions that may harm first responder medics (FRM) who are there to save the critically injured unstable people. FRMs must attend to those who would die without immediate medical attention and report to headquarters about what further resources are needed. This prevents FRMs from accomplishing their number one priority: save all the critically injured people. To attend to the time-sensitive injuries, FRMs must prioritize the order of which casualties they care for and minimize unproductive verification of death. In other words, the FRM does not want any potentially savable person to die while attending to someone who is already dead. Thus, knowing which casualties are already dead not only helps FRMs prioritize and maximize their medical expertise, it allows them to determine the total number of people who are alive and require attention by subtracting the number of deceased from the total number of bodies. This information helps the FRMs' second priority of informing headquarters of what additional rescue and medical supplies are needed. Based on these responsibilities, one of the current gaps appears to be that FRMs are unable to estimate death at a distance to avoid potentially deadly situations that may endanger their own safety. Such a distant decision-aid device with additional death determination capabilities may help FRMs better manage resources.

Dying is a process that varies over time. People who are alive have higher energy than deceased people. Physiological factors such as physical wellness and exertion create changes in the energy level over the living process. This leads to a much larger variance in energy fluctuation of living people relative to deceased people. Furthermore, the path each individual takes from a high energy life state to a low energy death state can vary drastically from person to person, causing a hysteresis loop. This phase transition phenomenon is analogous to a process in physics in which small magnetic domain walls re-adjust themselves under an increasing external magnetic field. As a result, the net magnetization varies, as does the dying process. In biology, the muscle response in lung tissue has demonstrated a hysteresis loop and people with chronic illnesses may get stuck in hysteresis with their health constantly cycling between high and low energy levels.

Some people may mistakenly declare death in the absence of detectable vital signs. This erroneous reasoning is due to the implicit bi-state assumption (if they are not alive, they are dead) and thus, negating the converse is not always right. In fact, there is a third category where a person who is not dead has no vital signs and these vitals can be restored with medical intervention, like resuscitation. Also, a person in a low energy state, e.g. comas, persistent vegetative states, or drug overdoses, may have feeble vital signs and are still alive, but in a unstable critical condition. This large variation of vitality signs may lead to false determinations of death. Thus, low energy indications of death are needed.

In nature, scavenger turkey vultures circulate over forests seeking dead rotten animals. How do birds locate, from above the forest trees, dead animals without seeing them? How do flies discover animals within minutes of death to lay fertilized eggs? They can smell death, which is known as peri-mortem (PM) odorants and which increases over time after death. The root cause of these volatile biomarker PM molecules is the cessation of white blood cell circulation, which leads to the buildup of bacterial byproducts. Bacteria proliferating without physiological inhibition and incomplete oxidation releasing reactive free radicals can break down large quantities of cellular tissues, releasing volatile byproducts in a PM plume around the body. Over time (days to years), PM molecules evolve into smaller post-mortem molecules, e.g. methyl mercaptan ($CH_3SH$). Thus, mortem signs are defined, in this disclosure, as the full molecular spectrum of volatile biomarker molecules from peri-mortem to post-mortem.

SUMMARY OF THE INVENTION

Multiple functional systems are integrated to configure a portable handheld decision-aid device for first responder medics (FRM). Fuzzy membership functions of "life" and "death" are used to determine the status of fallen people using remote measurements. State of the art EO/IR cameras can be used to detect and identify casualties in a mass injury situation, while also estimating body temperature. Using the temperature, along with the remote estimation of a second vital sign, the life membership proportion can be estimated from the ground truth by using a 2D projection of stable vital signs. The other fuzzy membership function, death, can be estimated by the presence or absence of peri-mortem and post-mortem molecules. These molecules are only released after death and provide a certain indication of death. Solid state UV laser resonance Raman backscattering from these molecules allows the device to analyze the molecules present in a plume around the casualty. Based on the results of a Boolean rule-based expert system, these fuzzy memberships allow remote determination of death. This information is displayed on a touch screen display that allows user input/output, as well as global positioning system (GPS) geo-location of the user and all identified casualties. Transceiver capabilities allow multiple FRMs to communicate and collaborate at the scene and transmit situational awareness reports back to headquarters so that medical logistics (personnel and supplies) can be managed. The ability of this device to identify deceased individuals from a remote (ball field) distance allows FRMs to maximize their medical attention to attend to the critically injured casualties without placing their own lives in danger from conditions such as crossfire and hostile baited traps.

An exemplary handheld portable device combines distant measurements of vital and mortem signs in joint membership sets based on a synergism between physics and physiology. The main vital signs are usually respiration rate (RR), heart rate (HR), blood pressure (BP), and temperature. Currently, laser vibrometery determines RR, radar micro-Doppler is used for HR, and body temperature is determined by Infrared images. FRMs also determine in-situ the neurophysiological responses, such as pupil reactivity to a shining blue pen light, muscle reaction to sharp poking stimuli, or hand-applied pressure to the neck for spinal nerve response. This set of measurements is not included in the current distant death consideration for two reasons: cessation of these measured vital signs helps but does not necessarily decide death of a specific body and the SWaP (size, weight and power) of these instrumentations is not yet compatible with a handheld device. Therefore, at a distance, incomplete vital signs become an open set that is difficult to quantify as useful death features.

In one aspect, such a decision-aid at a distance is a sensor-processor platform that fuses some useful features into a portable handheld device that uses resonant Raman ultraviolet (UV) laser (~240 nm wavelength) to identify a deceased individual from the plume backscattering. Cellular phone-like electro-optical/infrared (EO/IR) pin-hole cameras can take day/night images to automatically determine the geo-locations of warm bodies from the heat contrast signature in a colder environment. The device uses, together with entries of known scene landmarks and the location of the device, differential global positioning system (GPS) to triangulate the location of each body. Such a device can be equipped with an Inertial Guidance Unit (IGU) to further help the FRM accurately aim the Raman laser gun at the correct bearing angle to measure the plume backscattering intensity from the body. Thus, the ability to estimate plume molecules from a distance by Raman UV laser provides FRMs with a more accurate estimation of death.

In another aspect, a UV laser system can use compact solid state circuitry together with a smart Central Processing Unit (CPU). The CPU accesses a storage memory space where a list of backscattering spectrums is used to determine if any of the molecules present are PM or post-mortem. Since the open set of features cannot be normalized to the unit probability, a fuzzy membership function must be adopted to allow a crisp Boolean logic to address a rule-based lookup system. This is known in Artificial Intelligence as fuzzy logic and is used in this device to determine the likelihood of death. Additionally, the device can subtract from the EOIR cameras' estimation of the total number of immobile but warm bodies the number of deceased people to automatically order medical supplies from the headquarters. FRMs can use the system to re-organize the list of unstable critical people.

Mutual collaboration is possible through a cellular phone-like automatic wireless communication among FRMs and triage headquarters to provide situational awareness of the overall casualty scene. Currently, the digital wireless Medical Communication for Combat Casualty Care (MC4) is being used to link FRMs to a centralized database of military electronic medical records. The device is designed to be integrated with and made compatible to current MC4 hand-held devices.

BRIEF DESCRIPTION OF THE DRAWINGS

Additional advantages and features will become apparent as the subject invention becomes better understood by reference to the following detailed description when considered in conjunction with the accompanying drawings wherein:

FIG. 5 relates to remote estimation of vital signs in which two exemplary vital signs of blood pressure and temperature as remotely measured are tabulated.

FIG. 7 relates to an exemplary calculation of remotely measured vitals for an exemplary case of low blood pressure and high temperature, as seen on a 2D projection.

DETAILED DESCRIPTION

Figure 1:
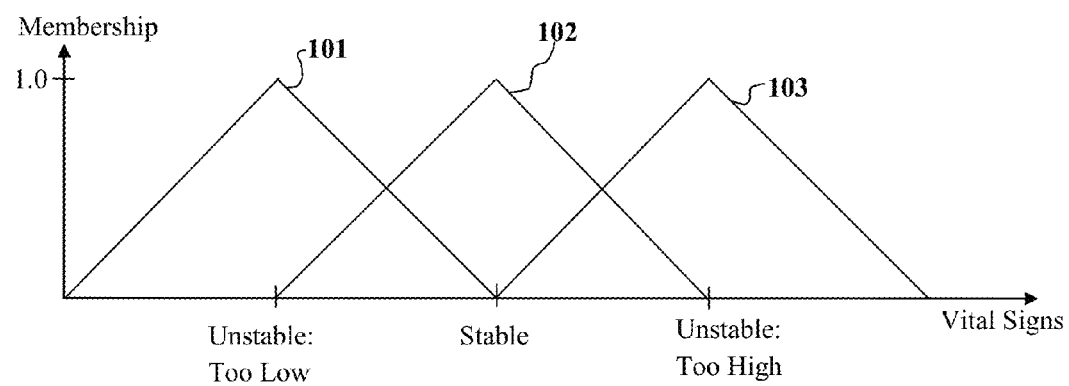
FIG. 1 illustrates exemplary ranges of stable and unstable vital signs in which vital signs must be within an optimal range to be stable.

Currently, first responders assess vital signs in-situ by measuring patients. FIG. 1 illustrates exemplary ranges of stable and unstable vital signs in which vital signs must be within an optimal range to be stable. Anything too high or too low results in unstable vitals and may indicate that there is something wrong with the person. Specifically, as shown in FIG. 1, if the vital sign falls within a certain range 102, then they have normal stable vitals. However, if the vital signs are too low, 101, or too high, 103, they are unstable because the body is not in equilibrium. Some essential vital signs include the four main vitals (HR, RR, BP, and temperature) and pupil reactivity. Other possible vital signs include pain, oxygen saturation, and reaction to painful stimuli.

Figure 2:
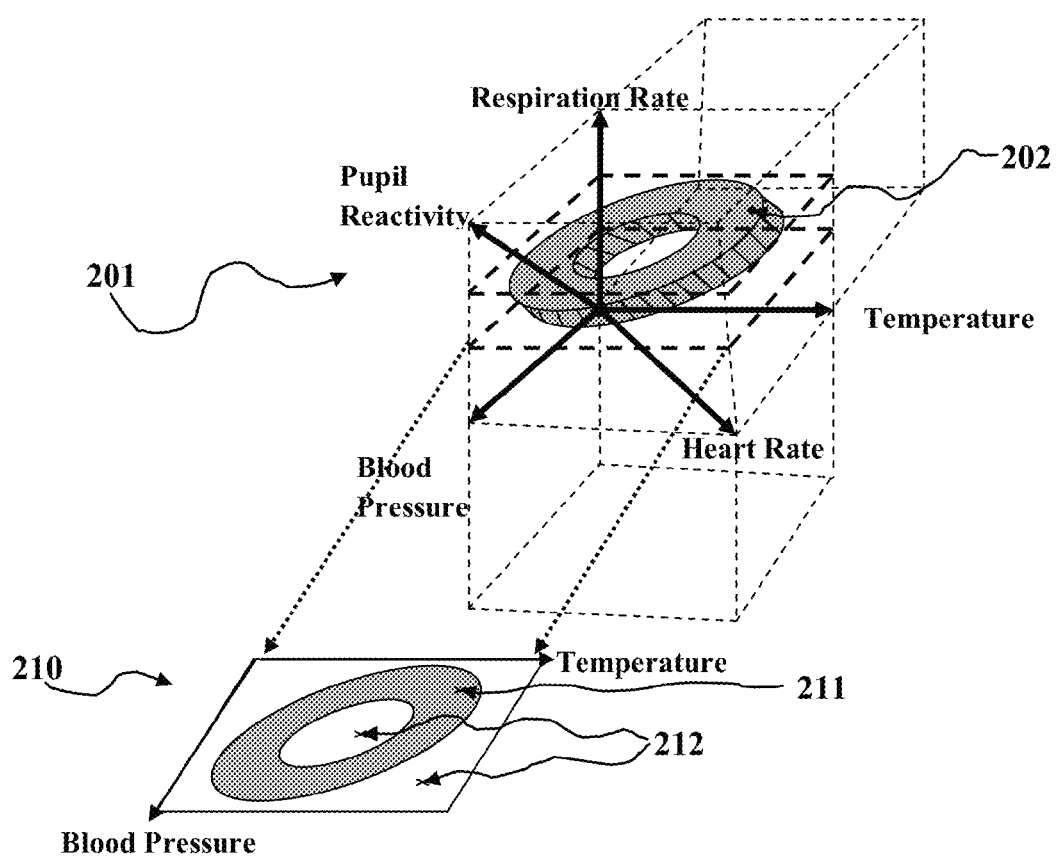
FIG. 2 shows an exemplary diagram illustrating exemplary ground truth vital signs as may be measured in-situ by medics and remote estimations.

FIG. 2 shows an exemplary diagram illustrating exemplary ground truth vital signs as may be measured in-situ by medics and remote estimations. This multi-dimensioned image is comprised of, e.g., 5 functions (respiration rate, pupil reactivity, blood pressure, heart rate, and temperature). If in-situ measurements are not feasible, remote estimations of vitals can be made by the 2D projection of the remotely measured features. Specifically, when the stable ranges for each of the vital signs are graphed on a single coordinate system, seen in FIG. 2, this creates a region 202 that indicates a person with stable vitals. This region represents ground truth measurements from medics. In order to accurately determine if a person falls within this stable region, the first responders must make in-situ measurements and evaluations of the person. To remotely estimate if a person has stable or unstable vitals, the healthy region 202 is projected onto a plane 210 that contains the signs that can be measured remotely. If the coordinates fall within the projection, the system assumes that the person most likely has stable vital signs.

Embodiment 1 shown in 210 uses body temperature and blood pressure to estimate if those values correspond to stable, 211, or unstable, 212, vital signs. These remote estimations can be obtained from infrared (IR) cameras and laser speckle. Quantitative IR cameras, or imaging radiometers, are able to determine the exact temperature of an object remotely. This allows the FRM to remotely estimate body temperature of the suspected casualty. When coherent light reflects off rough surfaces, it creates an interference known as laser speckle. This interference blurs the image; however, if something on or below the reflecting surface is moving, e.g. blood under skin, the motion can be tracked by the further blurring of the image. Knowing the lens geometry of the imaging camera, the blood flow velocity can be calculated by measuring the time it takes the increased blurriness to move across the field of view. From the conservation of energy, it is know that the sum of potential and kinetic energy will remain constant. (Constant=$P+\frac{1}{2}\rho_B v^2$). By occluding blood flow ($v=0$), the pressure measurement is equivalent to the constant. Once the constant is known, the measured blood flow velocity and constant can be used to estimate blood pressure. This estimation is valid due to the non-Newtonian flow characteristics of the viscoelastic rheology of blood.

Figure 3:
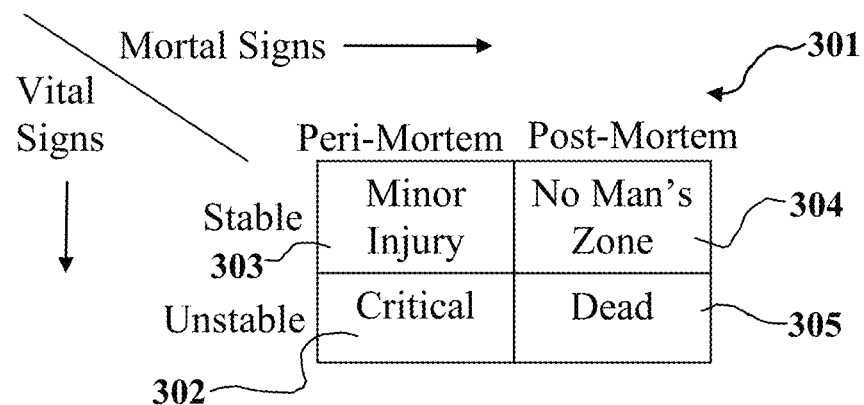
FIG. 3 shows an exemplary Boolean logic truth table used to determine the outcome status of a casualty.

Fuzzy logic (FL) is a method of determining membership when the boundaries between each group are unclear, ambiguous, and/or subjective. The logic behind the reasoning is clear; the boundaries between groups are not. Following a Boolean logic truth table, each input is placed in an output category. The FL system described below determines if a person is dead or not based on the vital and mortem signs recorded. FIG. 3 shows a crisp Boolean truth table 301 that indicates the relationship between vital and mortem signs. Such an exemplary Boolean logic truth table as shown in FIG. 3 can be used to determine the outcome status of a casualty. The inputs are stable and unstable vitals, along with peri-mortem and post-mortem molecules. The possible outcomes are minor injury 303, critical 302, dead 305, and no-man's zone 304.

Vital signs are high energy indications of life; mortem signs are low energy indications of death. While there are a large variety of vital signs that can be examined (HR, RR, BP, temperature, pain, eye pupil reactivity, nerve response, etc.), there are two main mortem signs: the release of peri-mortem (PM) and post-mortem molecules. These are molecules that result as the byproduct of bacteria or the cessation of blood flow and are released immediately upon death. Because blood flow has stopped, carbon dioxide waste accumulates in the blood, making the overall internal environment more reductive. This begins the decomposition process after death, which results in the production of volatile molecules. These gases escape through any opening in the body and form a plume around the dead body. The molecules released immediately after death are the larger PM ones. Over time, PM molecules break down and form smaller post-mortem molecules. As decomposition progresses, so does the amount of PM molecules generated and released therefore making the amount of PM molecules approximately proportional to the amount of time since death. Research has identified more than 400 decomposition odor molecules released weeks to years after death, making them post-mortem molecules. (See, e.g., Vass, Arpad, et. al., "Decompositional Odor Analysis Database," J. of Forensic Sci., Vol. 49, No. 4, July 2004.) Since mortem signs are unique indications of death, examining the combination of vital signs and mortem signs provide an accurate estimation of a person's status (alive or dead).

Looking at each individual combination in 301, the combination of stable vital signs and PM molecules, 303, indicates that the person is injured but stable. This is classified as a minor injury, which means that they do not require immediate attention from the FRM. Unstable vitals with PM molecules, 302, indicate a more serious injury that requires immediate attention. This is a critical injury which means the person may die if no immediate medical attention is provided. The first priority of FRMs is to attend to all these critical injuries. Therefore, this combination of vital and mortem signs is the most significant. The third possible case involves unstable vitals and post-mortem molecules, 305. This combination corresponds to death. Since post-mortem molecules are formed some time after death, their presence indicates that the person has been dead for awhile and medical attention will not help save them. This is an important category because if FRMs know who is already dead, they will not waste time verifying death while critically injured people who may be saved die. There is a fourth case: stable vital signs and post-mortem molecules, 304. However, this is not a feasible option since the presence of post-mortem molecules is an irrefutable indication that the person is dead. Therefore, they should not have stable vital signs. To indicate that this combination of inputs is not possible, 304 is referred to as "No Man's Zone." There is no category for uninjured people since they are mobile and can walk away after the incident. The measurements taken by the device are only on immobile bodies.

Figure 4:
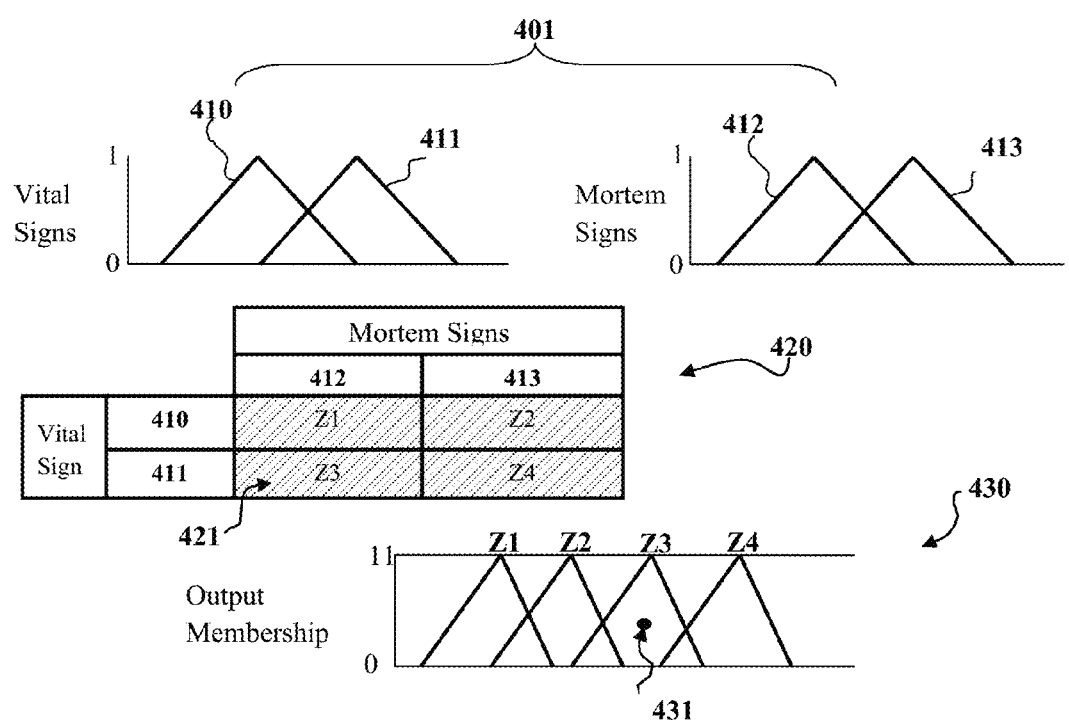
FIG. 4 relates to fuzzy logic calculation of output membership in which two exemplary inputs are graphed and the intersection of their values (minimum) is taken to determine the output membership.

By applying the truth table, 301, to the two inputs, the system is able to determine the output (status). FIG. 4 illustrates the process used to convert inputs into outputs. Specifically, FIG. 4 relates to fuzzy logic calculation of output membership in which two exemplary inputs are graphed and the intersection of their values (minimum) is taken to determine the output membership. The final status is identified by the location of the centroid. The two inputs, 401, are each comprised of two components. The vital signs of a person will be the percentage of stable, 410, and unstable, 411, features that are remotely determined by the device. This estimation is obtained by using FIG. 5, a table that calculates the overall stability of vital signs based on remote measurements of two vital signs, e.g. T and BP. Accordingly, FIG. 5 relates to remote estimation of vital signs in which two exemplary vital signs of blood pressure and temperature as remotely measured are tabulated. Likewise, the mortem signs input are comprised of two portions: PM molecule, 412, and post-mortem molecule, 413, concentration. The concentration of each is determined by a resonance Raman UV laser system, which analyses the intensity of the plume molecule backscattering. Using the proportions of each input segment (stable and unstable vitals, PM and post-mortem molecules), they are placed into the Boolean 2×2 truth table, 410, to calculate the intersection of the interaction. This is done by comparing each combination of vital and mortem sign and taking the minimum value. For example, 421 represents the outcome of unstable vital sign 411 and PM molecule 412. The values of 411 and 412 are compared and the system takes the smaller proportion value to be the output value Z3 in 421. The completed table 410 corresponds to the logic truth table 310, with each Z value corresponding to an output status (minor injury, critical, dead, and no man's zone).

Every Z value calculated on table 420 is then graphed onto the output membership graph 430. For example, the proportion value given 421 is used to shade in the same proportion in 431, which is the Z3 output value (critical). After the output membership function 430 has been determined, the location of its centroid indicates what the final output is.

Figure 6:
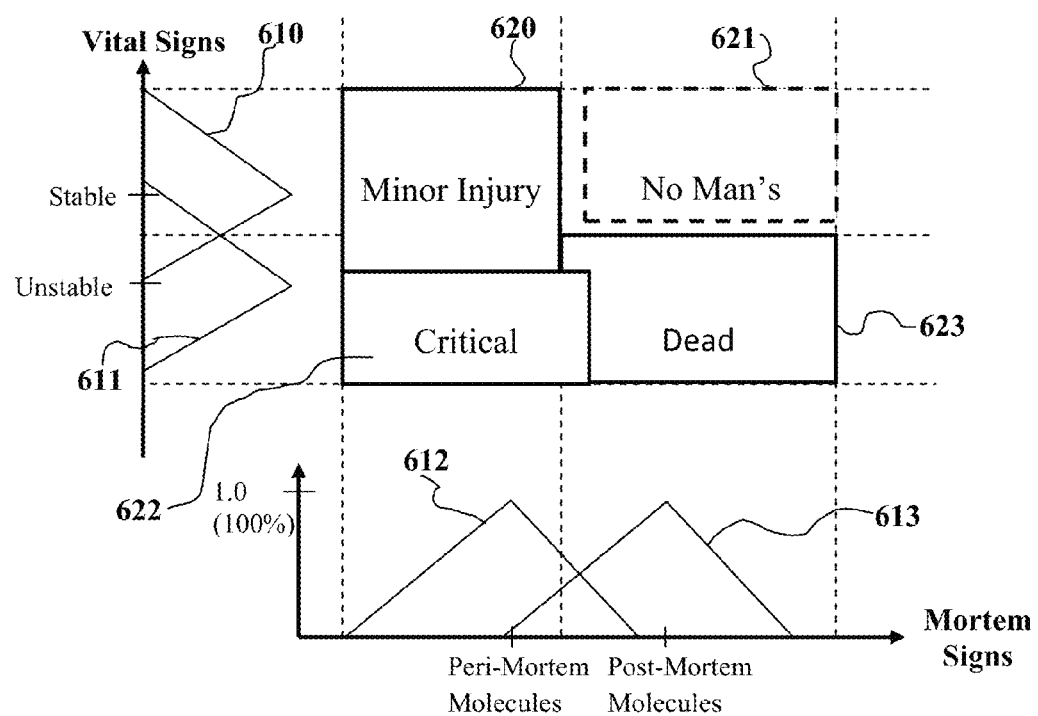
FIG. 6 illustrates exemplary remotely measured vital and mortem signs by Medics.

A graphical representation of this method is shown on FIG. 6. Specifically, FIG. 6 illustrates exemplary remotely measured vital and mortem signs, e.g., by medics. Stable 610 and unstable 611 vital signs are graphed on the vertical axis while PM molecules 612 and post-mortem molecules 613 are graphed on the horizontal axis. The output is determined by taking the two inputs as the coordinates of the outcome. The estimation of stable and unstable vitals obtained from FIG. 5 determines the one coordinate while the proportion of peri- and post-mortem molecules specifies a second coordinate. Taken together, these two coordinates indicate a point location in the output function as a minor injury 620, a critical injury 622, a dead person 623, or in no man's zone 621.

Figure 8:
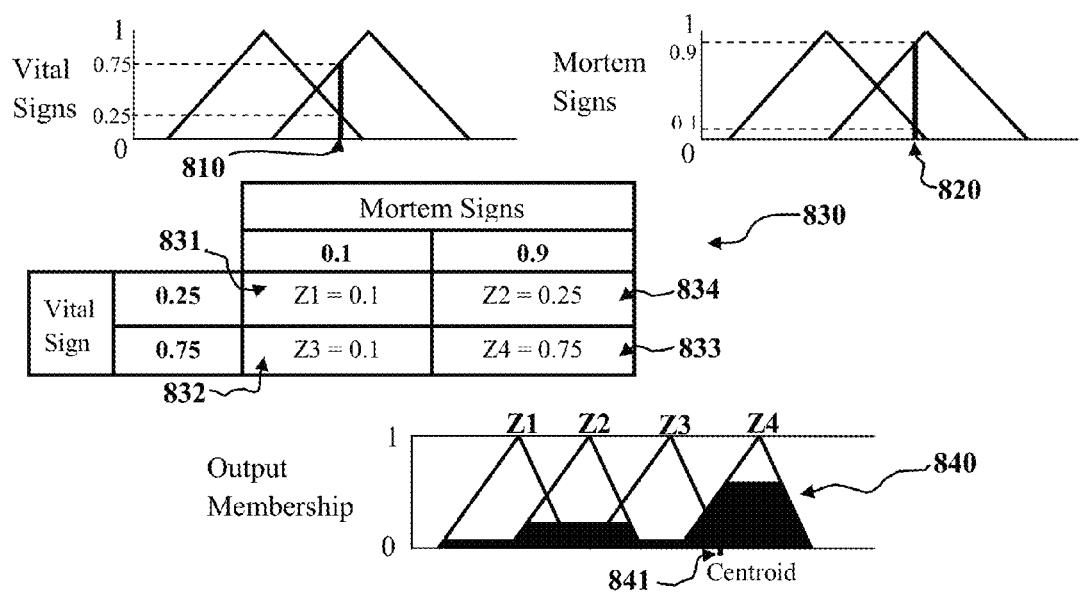
FIG. 8 relates to an exemplary fuzzy logic calculation based on the exemplary tabulation shown in FIG. 7.
Figure 9:
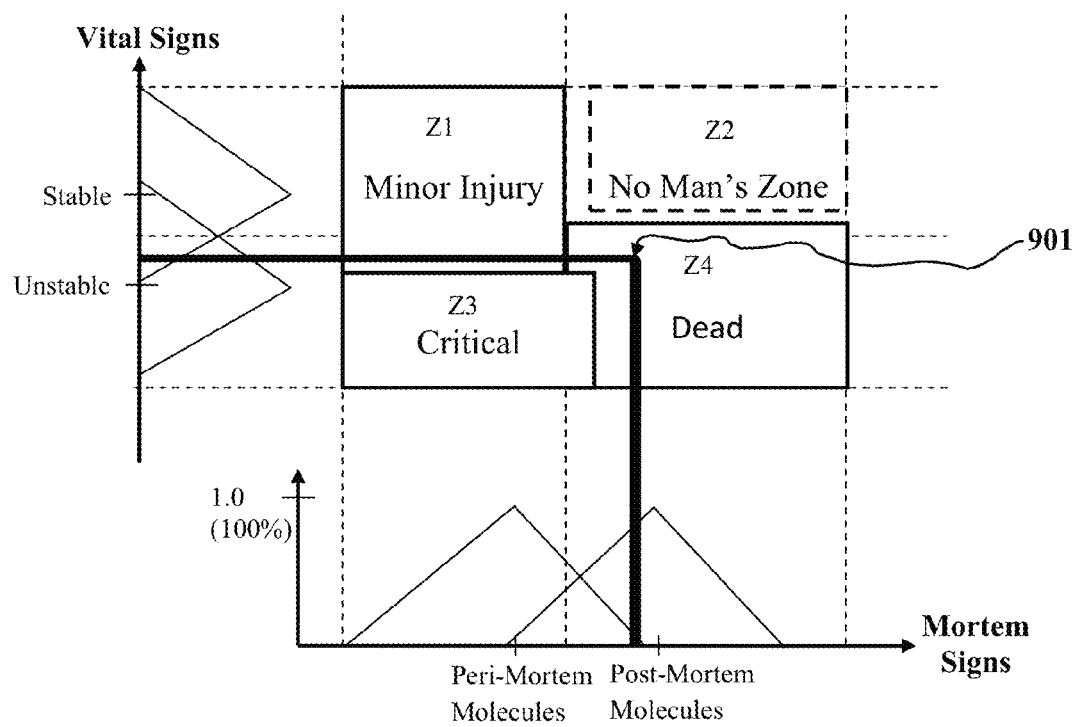
FIG. 9 relates to mapping of fuzzy logic which illustrates the graphical relationship of the FIG. 7 exemplary inputs to the calculated output status.

FIGS. 7, 8, and 9 show a sample calculation. For example, FIG. 7 relates to an exemplary calculation of remotely measured vitals for an exemplary case of low blood pressure and high temperature, as seen on a 2D projection. If the device remotely estimates that the blood pressure is between 12.0/8.0 to 13.3/8.7 kPa (systolic/diastolic) and body temperature is greater than 104° F., this leads to a person with 25% stable and 75% unstable vital signs. This is found by using FIG. 7 to find the intersection of the blood pressure and temperature measured. This value represents an estimation of vital signs. If plotted on the 2D projection of stable and unstable vital signs 710, the person with the previously given pressure and temperature would fall, e.g., at 711 on the graph. With such a high temperature and low blood pressure, they have mostly unstable vitals.

FIG. 8 illustrates how this example would be calculated to determine the outcome status of the person. More specifically, FIG. 8 relates to an exemplary fuzzy logic calculation based on the exemplary tabulation shown in FIG. 7. Since the exemplary blood pressure and temperate combination gives a 25% stable and 75% unstable vital combination, this is represented by the 810. If the resonance Raman measurement resulted in a reading of 90% post mortem molecules and 10% PM molecules, this would be represented by 820. Taking the proportions of each (0.25 stable vital, 0.75 unstable vital, 0.1 PM molecule, 0.9 post-mortem molecule), the 2×2 table 830 is used to determine the intersection of the functions. 831 is the minimum of stable vitals and PM molecules, which is 0.1 (see, e.g., 832) is the minimum of unstable and PM (see, e.g., 833) the minimum of unstable vitals and post-mortem, and 834 the minimum of stable vitals and post-mortem. This results in the output membership proportions of Z1=0.1, Z2=0.25, Z3=0.1, and Z4=0.75. When graphed onto the output membership, it results in the graph 840. Taking the mean of the output function gives the location of the centroid 841. This location (Z1, Z2, Z3, or Z4) determines what the output status is. In the example, the centroid is located in Z4, which corresponds to dead, which means that a person with the given vital and mortem signs is dead. The same outcome is shown in FIG. 9, in which 901 is the intersection of the two input memberships. Specifically, FIG. 9 relates to mapping of fuzzy logic which illustrates the graphical relationship of the FIG. 7 exemplary inputs to the calculated output status. (The final outcome exemplified in FIG. 9 is intended to match the centroid in FIG. 8.) The same lines as shown in 810 and 820 are simply graphed perpendicular to each other to determine the intersection, which lies in the Z4 or dead region.

Figure 10:
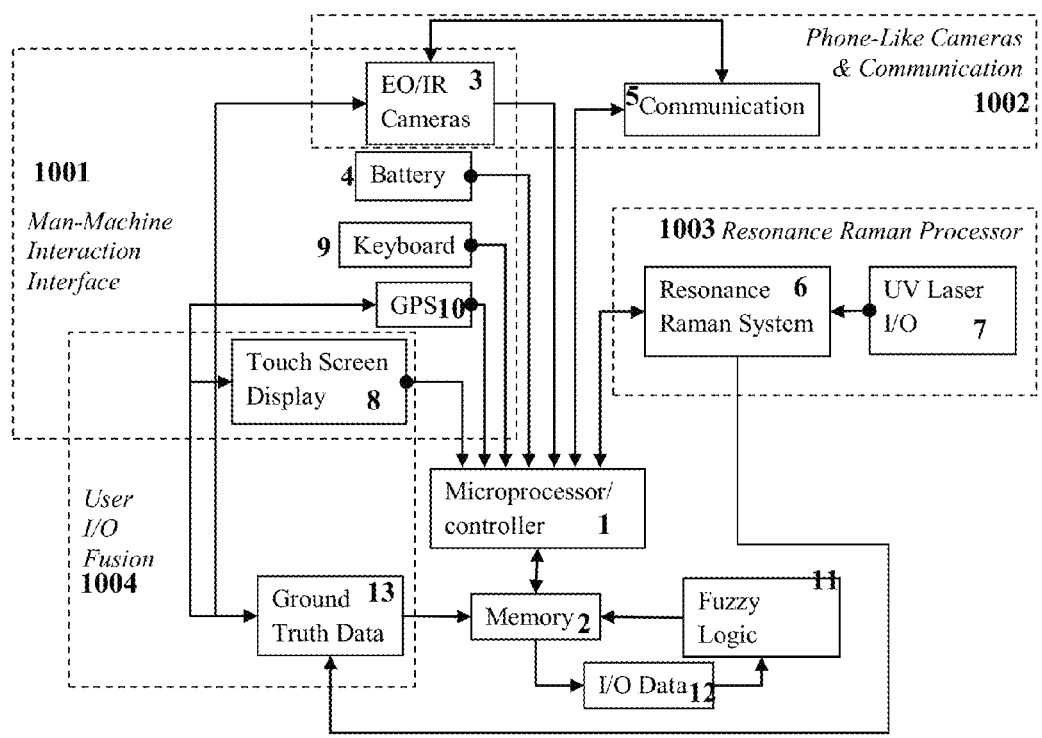
FIG. 10 illustrated an integrated system of multiple functional devices in which exemplary hardware and software are configured with phone-like cameras and communication, a man-machine interaction interface, and the user I/O fusion.

FIG. 10 shows an exemplary circuit block diagram of the device. Specifically, FIG. 10 illustrated an integrated system of multiple functional devices in which exemplary hardware and software are configured with phone-like cameras and communication, a man-machine interaction interface, and the user I/O fusion. Additional components include the Resonance Raman Processor, the CPU, memory, and fuzzy logic rule table. A smart CPU 1 controller integrates all the components into one device. An example is the Intel Xeon with up to 8 multi-core capabilities. This has eight connections to other components in the circuitry. Additional memory 2 is used to increase computing speed and store items such as the fuzzy logic tables 11, lists of PM and post-mortem molecules, and past input/output (I/O) data 12. One possible memory module is the small outline dual in-line memory module (SO-DIMM). An example of a SO-DIMM strip would be the Micron 2 GB DDR3 RAM.

Another component attached to the CPU is two cell-phone-like cameras 3 that will take day and night photos. Some possible embodiments include the OmniVision OV14810-A16A camera chip for day images and the circuitry from the FLIR i7 Infrared camera for night images. A communication chip 5 is connected to both the CPU and the EO/IR cameras. A possible transceiver is the OneChip Photonics Gigabit Passive Optical Network SFP OLT. These two parts, 3 and 5, make up the phone-like cameras and communication component of the device 1002.

The EO/IR cameras 3 are also part of the man-machine interaction interface 1001. Other components in this interface include the battery 4, keyboard 9, GPS 10, and touch screen display 8. Each of the components in 1001 is also connected to the CPU 1. The EO/IR cameras use the day/night images to automatically determine the possible locations of casualties by their warm heat signature compared to the colder environment. These locations are marked on the touch screen display 8 of maps. The GPS takes these locations and triangulates the exact geo-location using the known position of the device and any known scene landmarks. A terrain map with the marked geo-location can be accessed on the touch screen so that medics know which direction each body is located in. The battery is used to power the device, including the keyboard and touch screen display.

A User I/O fusion 1004 allows ground truth data 13 to be entered by the user on the touch screen display 8. The ground truth data 13 is obtained from the EO/IR cameras 3, GPS 10, and information entered manually by the user on the touch screen display 8. In future generations of the device, the user can confirm the life/death decision determined by the user. The information will be stored in the memory 2 for future use.

The last major component of the device circuitry is the Resonance Raman Processor 1003, which is comprised of the resonance Raman System 6 and a solid state UV laser I/O 7. The laser, such as a RPMC FP-2 solid state 266 nm Nd:YAG microchip laser, is used to obtained the correct resonant Raman frequency needed for the PM molecules. This 4th harmonic laser can be pulsed to obtain to the correct resonance frequency needed to detect PM and post-mortem molecules. The Raman system 6 measures the inelastic backscattered light from the UV laser hitting the plume molecules. Such a system could use a Raman Spectrometer microsystem on a chip. (See, e.g., U.S. Pat. No. 7,505,128 B2 Zribi et al.) When light hits a molecule, a minute amount is reflected back at a different frequency. The difference between the incidence light and the backscattered light, known as the Raman shift, is unique for each molecule. In resonance Raman, the incidence light's frequency is adjusted so that the scattered light corresponds to the molecule's electronic transition energy. This makes the intensity of the Raman backscattering up to 104 times larger and allows the minute amounts to be detected. After the Raman system has measured the plume backscattering, it accesses a library of known molecular spectrums to determine the identity and concentration of the molecules present. The information is then sent to the CPU, which contains a list of PM and post-mortem molecules stored in memory, to determine if the molecules present are mortem signs.

To determine if the person is dead or alive, the device uses the information from the Resonance Raman Processor 1003 (which remotely measures mortem signs) and the EO/IR cameras (which remotely measures vital signs) as inputs in a fuzzy logic rule based table 11 that is stored in memory 2. These rules are set and are used to define what the output status is based on the inputs (as shown in FIG. 4) In this design, the I/O data is used in the Boolean truth table to determine the outcome. In future embodiments, the fuzzy logic evolves with the data to sharpen the boundary lines between the decisions so that a no-man's zone decision does not occur. This method would use the I/O data, which is later verified by the user, to modify the fuzzy logic rules based on ground truth data.

Figure 11:
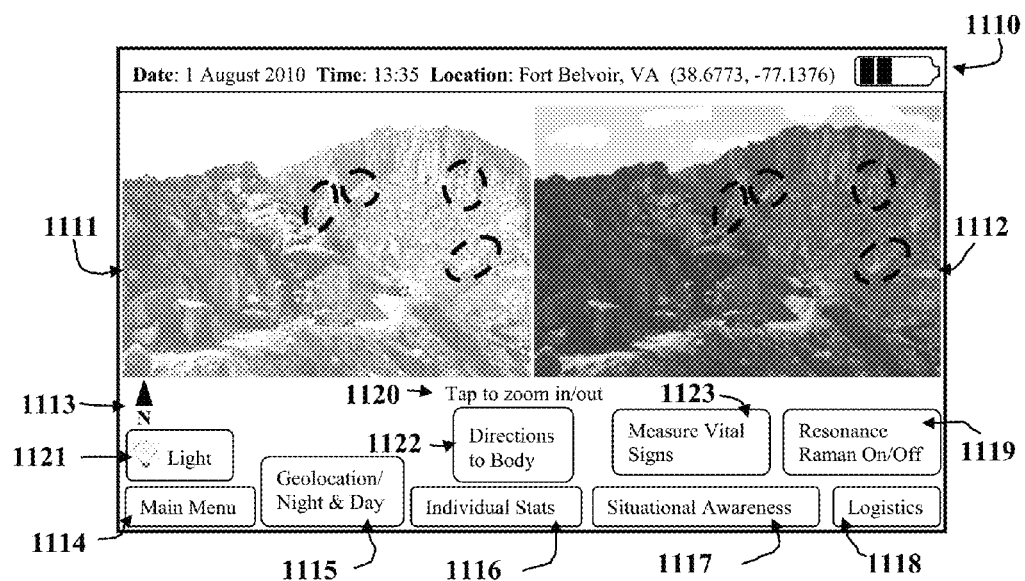
FIG. 11 relates to a device display of night and day images in which an exemplary touch screen display is shown for the EO/IR cameras' day/night imagery.

FIG. 11 shows the EO/IR display mode of the device. Specifically, FIG. 11 relates to a device display of night and day images in which an exemplary touch screen display is shown for the EO/IR cameras' day/night imagery. Also exemplified are the situational awareness top bar and the navigation buttons on the bottom. The image represents the touch screen display that the user will see after the cameras are initiated to take 2D projections of the land. The EO camera produces a day image 1111 while the IR camera gives a night image 1112. Together, the device is able to automatically mark the location of possible casualties from their heat signature. Since human bodies take at least a day to cool to ambient temperature, the infrared cameras can identify bodies from the colder environment. The possible location of casualties is marked in both 1111 and 1112. Instructions 1120 under the day/night images give additional information to the user, in this situation, letting them know how to change the resolution of the image. Another feature included in this view is a compass 1113 which indicates the direction of north on the images.

Some common features across every display screen are the top bar with important information such as date, time, and location, and the buttons along the bottom of the screen. The top bar 1110 contains the date, location in words and latitude/longitude, and the battery status. This bar automatically updates with the device's location and local time using satellite signals from the GPS. The location is also given in latitude and longitude for more precise geo-location. The battery image reflects the amount of energy left in the battery before it must be recharged. Some of the buttons along the bottom of the screen are for a screen backlight 1121, the main menu 1114, a toggle between geo-location and EO/IR view 1115, an individual statistics 1116, situational awareness summary 1117, logistics summary 1118, resonance Raman system power button 1119, vital sign measurements button 1123, and a button to provide directions to a body 1122. These buttons are always present.

The light button 1121 turns on a small backlight so that the display can be visible in dark or obscured conditions. The main menu 1114 takes the user to a list of all possible functions of the device. Individual statistics 1116 list the injury and medical information for each patient. The file is started when remote measurements are taken and recorded for each body. When the FRM eventually attends to the casualties, the rest of the file, including personal information and injury information, is updated. The situational awareness button 1117 takes the user to a screen summarizing the scene, breaking down each casualty into the possible categories (dead, critical, minor injury) and listing the geo-location for each one. Additionally, a summary of the supplies needed to care for all the people who are not dead is listed. The logistics 1118 function displays a more detailed listing of what medical supplies and help is needed. This also reflects how much aid the headquarters will send after they review the current situation and the additional needed supplies.

The Resonance Raman On/Off button 1119 powers on the laser for remote estimations of mortem signs. When powered on, the Raman system shines a laser in the aimed direction. This system measures the backscattered light from the plume around each body and identifies if any PM or post-mortem molecules are present. The measure vital signs button 1123 is used to trigger remote estimations of vital signs, in this embodiment, measuring temperature from infrared cameras and blood pressure from laser speckle. The "directions to body" 1122 allows the user to identify one of the marked bodies and obtain directions from their current location to the body. In FIG. 11, the display shows the Night/Day images. To change the view to the geo-location map, the user can hit the geo-location/Night & Day button 1115 to toggle the function.

Figure 12:
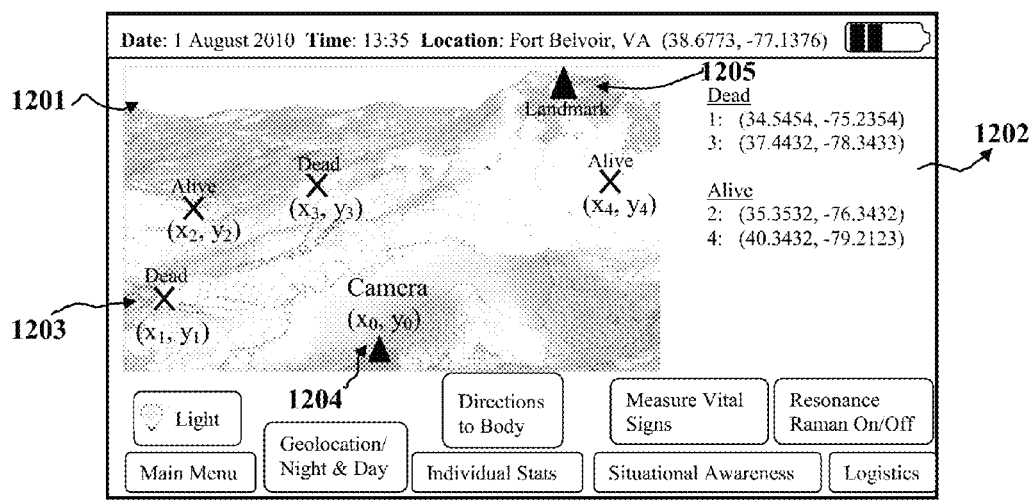
FIG. 12 relates to a device display of geo-location functionality showing an exemplary touch screen display for the geo-location function of the device.

FIG. 12 is an exemplary geo-location display view, which has the common top bar information and functional choice buttons along the bottom. Specifically, FIG. 12 relates to a device display of geo-location functionality showing an exemplary touch screen display for the geo-location function of the device. Each casualty location and status is marked, along with the camera's location and known landmarks, on a terrain map. In the geo-location view, there is a terrain map 1201 that depicts out the current scene with elevation and landmarks. The location of the camera, and thus the user, is marked on the map 1204. Any known scene landmarks, such as buildings or telephone poles, are also marked and its geographical location noted 1205. Using the known locations of 1204 and 1205, the GPS can triangulate the location of each body. These bodies are identified on the terrain map with their geographical coordinates and status 1203. This information is also listed on the screen, 1202, sorted by status (dead, alive).

Figure 13:
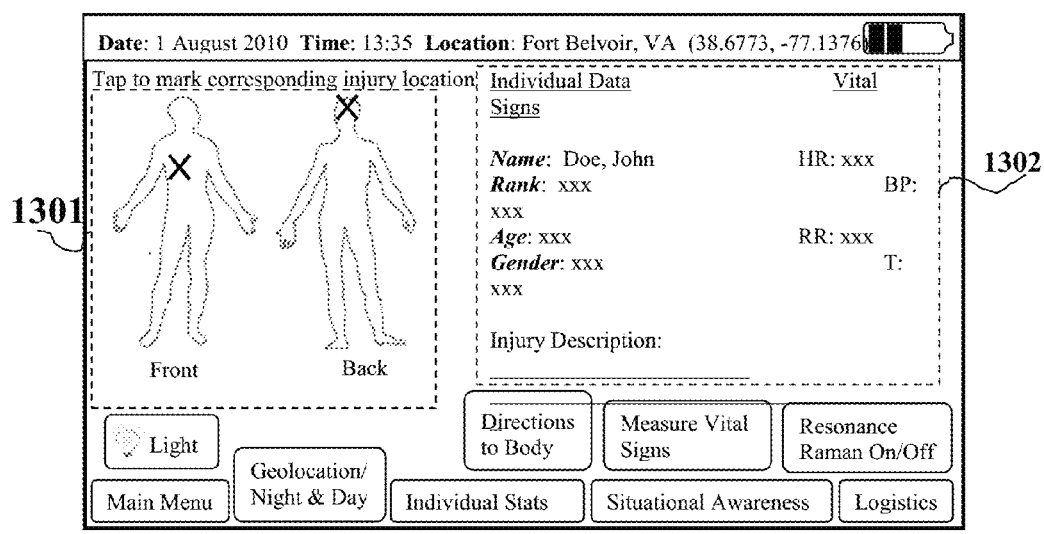
FIG. 13 relates to a device display of individual injury report, and it shows an exemplary touch screen display for individual data entry.

FIG. 13 is a representation of the individual stats mode, which records a person's vital and mortem signs, injury location and treatment, and personal information. FIG. 13 relates to a device display of individual injury report, and it shows an exemplary touch screen display for individual data entry. This includes the remote estimations of vital and mortem signs, as well as personal information and injury location, description, and treatment, which are all updated when the FRM attends to the casualty. This format is compatible with the MC4 system currently being used and can eventually be integrated. Two outlines of a body on the left side of the screen 1301 are used to represent the front and back of a person. When the FRM attends to a casualty, they can touch the screen to mark the location of any injuries to the person. Individual data is entered on the left side of the screen 1302. This includes remote estimations of vital and mortem signs. After a FRM has checked the person, they can enter in the wound location, description, and treatment. Additionally, personal information is logged so that the person's health records can be updated at a future point in time.

Figure 14:
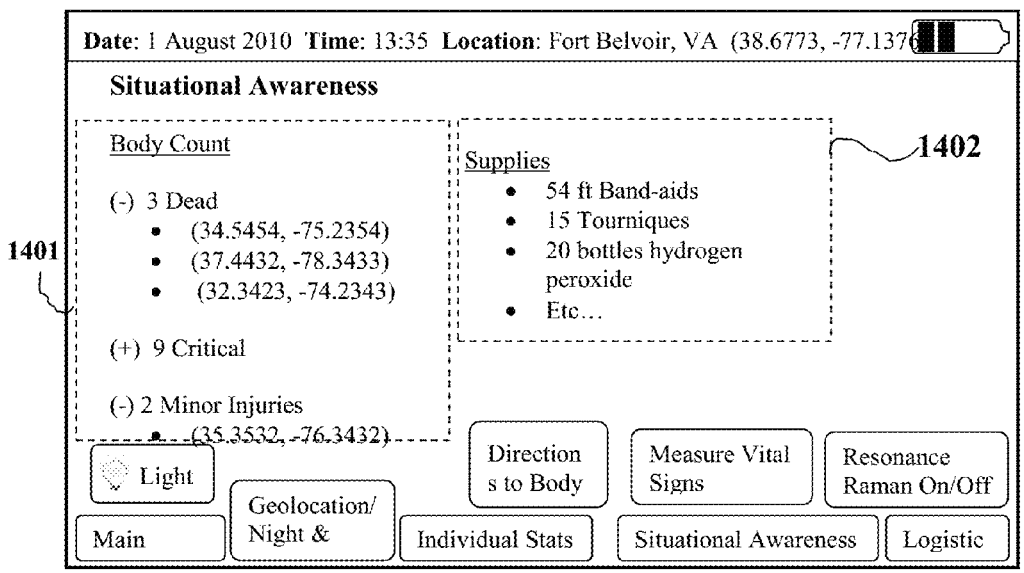
FIG. 14 relates to a device display of summary situational awareness report in which an exemplary touch screen display is shown for the situational awareness summary.

FIG. 14 shows a situational awareness summary. FIG. 14 relates to a device display of summary situational awareness report in which an exemplary touch screen display is shown for the situational awareness summary. This lays out the body count by status and geo-location. Such a device can also automatically determine the number of supplies needed to attend to all the people who are not dead. 1401 contains the total body count, listing each casualty by geo-location and status. This page can help the FRM better identify which order to attend to the casualties to maximize their impact. Also included in the situational awareness is an estimation of the total supplies needed to treat all the people who are not dead 1402. This information is calculated automatically by the device and is transmitted to headquarters by the transceiver for the final determination of what additional aid is needed.

It is obvious that many modifications and variations of the present invention are possible in light of the above teachings. It is therefore to be understood that within the scope of the appended claims, the invention may be practiced otherwise than as described.

What is claimed is:

1. A situational awareness apparatus based on a hand-held Raman laser device integrating multiple functional systems for distant life-death determination, the apparatus comprising:
    a laser resonance Raman backscattering device;
    a set of day & night EO/IR cameras capable of high resolution imaging;
    a user I/O fusion capability to take into account first responder medics knowledge and/or ground truth obtained from a touch screen and said set of EO/IR cameras to determine remotely estimated and final decisions of first responder medics;
    a signal-to-noise enhancement processing system configured to measure an effluent plume of peri-mortem and post mortem molecules based on said laser resonance Raman backscattering device;
    a smart storage firmware, CPU, and I/O device with memory to compute a process to identify molecules present and their concentration based on a spectral library of known molecules, wherein said process incorporates:
        stored updatable molecular spectrum library of peri-mortem and post-mortem laser backscattering data for identifying mortem fuzzy membership function, and/or
        stored fuzzy logic rule based 2×2 tables to combine vital and mortem signs based on remote estimations; and
    a touch-screen interface comprising a programmable firmware to display situational awareness results based on said process and accomplish a fine resolution geo-location grid touch screen, wherein data from the Raman backscattering device and the IR camera are inputted to the fuzzy logic to determine an outcome.

2. The situational awareness apparatus according to claim 1, wherein said touch-screen interface is of a display device comprising:
    display of date, time, geographical coordinates, and battery power;
    display choice buttons to navigate among various options;
    display of each body injury case data compatible with a medical communication for combat casualty care; and
    display of a situational awareness summary report in terms of body count as to life or death, and the additional supplies and the first responder medic personnel needs to be sent or transmitted to headquarters.

3. The situational awareness apparatus according to claim 1, comprising at least one of a cellular phone and hardware imaging and wireless communication technology to provide situational awareness to users.

4. The situational awareness apparatus according to claim 1, wherein a plurality of users are first responder medics and/or their commanding headquarters.

5. The situational awareness apparatus according to claim 1, wherein said touch-screen interface is capable of standard display and keyboard interfaces to interface with at least one of:
    a set of EO/IR cameras to obtain overall scene imagery and identify possible casualties;
    GPS to triangulate the location of possible casualties using the known location of the camera and known scene landmarks;
    a keyboard to input more information into the system; and
    a diesel or solar rechargeable electrical battery to operate the device in a mass casualty field or battlefield.

6. The situational awareness apparatus according to claim 1, wherein said set of day & night EO/IR cameras are based on a miniaturized cellular phone imaging and secured wireless communication technology, comprising:
    high resolution imaging cameras with a sufficient human body resolution for distances over a 100 meter squared ball field area; and
    private and secured wireless broadcasting transceiver among each hand-held laser backscattering device for collaboration among users.

7. The situational awareness apparatus according to claim 1, wherein said signal-to-noise enhancement processing system is on a chip to implement a method of measuring an effluent plume of peri-mortem and post mortem molecules.

8. The situational awareness apparatus according to claim 1, wherein said laser resonance Raman backscattering device comprises:
    a battery-operated and portable microchip laser using 4th to 5th harmonics solid state glass laser Neodymium Yttrium Aluminum Garnet producing 240 nm UV coherent light at 1+Watt for determination of mortem molecular spectrum of a small plume around a body; and
    a system to receive backscattered light for said identification of molecules present and their concentration.

9. A multi-functional integrated decision-aid system for first responder medics to determine status of fallen people using remote measurements of a situational awareness apparatus based on fuzzy membership functions of life and death, the system comprising the following process steps:
    using EO/IR cameras to detect, identify and/or estimate a body temperature of a casualty in a mass injury situation;
    analyzing a solid state UV laser resonance Raman backscattering from peri-mortem and post-mortem molecules present in a plume around said casualty;
    remotely determining death based on the results of a Boolean rule-based expert system using fuzzy memberships, wherein death is estimated as a fuzzy membership function by the presence or absence of peri-mortem and post-mortem molecules; and touch-screen display of input/output information using global positioning system geo-location of said apparatus to remotely determine a death state of said casualty.

10. The multi-functional integrated decision-aid system according to claim 9, comprising a 2D projection of stable vital signs to deduce a ground truth.

11. The multi-functional integrated decision-aid system according to claim 9, wherein said peri-mortem and post-mortem molecules are released after death for the remote determination of death.

12. The multi-functional integrated decision-aid system according to claim 9, comprising transceivers to allow multiple first responder medics to communicate and collaborate and transmit situational awareness reports so that medical logistics can be managed.

13. The multi-functional integrated decision-aid system according to claim 9, wherein said remote identification of a death state of said casualty facilitates first responder medics to better identify deceased casualties without placing their own lives in danger from conditions such as crossfire and hostile baited traps, and more effectively provide medical attention to those who are critically injured.

14. The multi-functional integrated decision-aid system according to claim 9, wherein said body temperature along with a remote estimation of a second vital sign are used to estimate a life membership proportion as aided by a ground truth.

\* \* \* \* \*